United States Patent
Nobles et al.

(10) Patent No.: US 10,178,993 B2
(45) Date of Patent: Jan. 15, 2019

(54) DEVICE AND METHOD FOR ASSISTING END-TO-SIDE ANASTOMOSIS

(71) Applicant: CARDIO MEDICAL SOLUTIONS, INC., Fountain Valley, CA (US)

(72) Inventors: Anthony A. Nobles, Fountain Valley, CA (US); Benjamin G. Brosch, Mission Viejo, CA (US)

(73) Assignee: Cardio Medical Solutions, Inc., Fountain Valley, CA (US)

( * ) Notice: Subject to any disclaimer, the term of this patent is extended or adjusted under 35 U.S.C. 154(b) by 594 days.

(21) Appl. No.: 14/795,146

(22) Filed: Jul. 9, 2015

(65) Prior Publication Data

US 2016/0007998 A1 Jan. 14, 2016

Related U.S. Application Data (60) Provisional application No. 62/023,719, filed on Jul. 11, 2014.

(51) Int. Cl.
*A61B 17/11* (2006.01)
*A61B 17/00* (2006.01)
(Continued)

(52) U.S. Cl.
CPC .......... *A61B 17/11* (2013.01); *A61B 17/0057* (2013.01); *A61B 17/1204* (2013.01); *A61B 17/12109* (2013.01); *A61B 17/12131* (2013.01); *A61B 2017/00659* (2013.01); *A61B 2017/00876* (2013.01); *A61B 2017/1107* (2013.01);
(Continued)

(58) Field of Classification Search
CPC .......... A61B 17/0057; A61B 17/12109; A61B 17/11; A61B 17/1204; A61B 17/12131; A61B 2017/00659; A61B 2090/0811; A61B 2017/1135; A61B 2017/00876; A61B 2017/1107
See application file for complete search history.

(56) References Cited

U.S. PATENT DOCUMENTS

| 4,744,364 A | 5/1988 | Kensey |
| 4,774,091 A | 9/1988 | Yamahira et al. |

(Continued)

FOREIGN PATENT DOCUMENTS

| EP | 0 544 485 | 6/1993 |
| EP | 0 894 475 | 2/1999 |

(Continued)

OTHER PUBLICATIONS

Cardio Medical Solutions, Inc. brochure titled: "Baladi Inverter for Clamp less Surgery"—Undated.
(Continued)

*Primary Examiner* — Son Dang
(74) *Attorney, Agent, or Firm* — Knobbe, Martens, Olson & Bear, LLP (57) ABSTRACT

Disclosed herein are embodiments of devices and methods for forming a seal covering an incision in tissue. In some embodiments, a deformable member can be loaded into a catheter and inserted into the tissue incision. The deformable member can unfold into a cup-shape which can form a seal around the incision during a procedure. Once the procedure is finished, the deformable member can be drawn back into the tube.

16 Claims, 10 Drawing Sheets

US 10,178,993 B2
Page 2

(51) Int. Cl.
*A61B 17/12* (2006.01)
*A61B 90/00* (2016.01)

(52) U.S. Cl.
CPC ............ *A61B 2017/1135* (2013.01); *A61B 2090/0811* (2016.02)

(56) References Cited

U.S. PATENT DOCUMENTS

| | | | |
|---|---|---|---|
| 4,794,928 A | 1/1989 | Kletschka | |
| 5,122,122 A | 6/1992 | Allgood | |
| 5,192,301 A | 3/1993 | Kamiya et al. | |
| 5,222,974 A | 6/1993 | Kensey et al. | |
| 5,290,249 A | 3/1994 | Foster et al. | |
| 5,330,446 A | 7/1994 | Weldon et al. | |
| 5,330,497 A | 7/1994 | Freitas et al. | |
| 5,342,393 A * | 8/1994 | Stack | A61B 17/0057 24/453 |
| 5,350,399 A | 9/1994 | Erlebacher et al. | |
| 5,370,685 A | 12/1994 | Stevens | |
| 5,383,896 A | 1/1995 | Gershony et al. | |
| 5,395,383 A | 3/1995 | Adams et al. | |
| 5,423,777 A | 6/1995 | Tajiri et al. | |
| 5,447,515 A | 9/1995 | Robicsek | |
| 5,496,332 A | 3/1996 | Sierra et al. | |
| 5,527,338 A | 6/1996 | Purdy | |
| 5,540,658 A | 7/1996 | Evans et al. | |
| 5,593,422 A | 1/1997 | Muijs Van de Moer et al. | |
| 5,630,833 A | 5/1997 | Katsaros et al. | |
| 5,637,097 A | 6/1997 | Yoon | |
| 5,690,674 A | 11/1997 | Diaz | |
| 5,700,277 A | 12/1997 | Nash et al. | |
| 5,749,883 A | 5/1998 | Halpern | |
| 5,766,220 A | 6/1998 | Moenning | |
| 5,846,251 A | 12/1998 | Hart | |
| 5,853,399 A | 12/1998 | Sasaki | |
| 5,853,422 A | 12/1998 | Huebsch et al. | |
| 5,944,730 A | 8/1999 | Nobles et al. | |
| 5,951,588 A | 9/1999 | Moenning | |
| 6,171,319 B1 | 1/2001 | Nobles et al. | |
| 6,352,543 B1 * | 3/2002 | Cole | A61B 17/0057 128/898 |
| 6,395,015 B1 | 5/2002 | Borst et al. | |
| 6,409,739 B1 | 6/2002 | Nobles et al. | |
| 6,537,299 B1 | 3/2003 | Hogendijk et al. | |
| 7,931,641 B2 * | 4/2011 | Chang | A61B 17/3415 604/540 |
| 8,398,676 B2 * | 3/2013 | Roorda | A61B 17/0057 606/213 |
| 8,500,776 B2 * | 8/2013 | Ebner | A61M 1/0088 606/151 |
| 8,623,036 B2 * | 1/2014 | Harrison | A61B 17/11 606/153 |
| 8,728,105 B2 * | 5/2014 | Aguirre | A61B 17/1114 606/153 |
| 9,332,976 B2 * | 5/2016 | Yribarren | A61B 17/0057 |
| 9,364,238 B2 * | 6/2016 | Bakos | A61B 17/1114 |
| 9,402,605 B2 * | 8/2016 | Viola | A61B 17/0057 |
| 2002/0169475 A1 * | 11/2002 | Gainor | A61B 17/0057 606/213 |
| 2002/0183787 A1 * | 12/2002 | Wahr | A61B 17/0057 606/213 |
| 2003/0220667 A1 * | 11/2003 | van der Burg | A61B 17/0057 606/200 |
| 2004/0102797 A1 | 5/2004 | Golden et al. | |
| 2005/0033361 A1 | 2/2005 | Galdonik et al. | |
| 2008/0065145 A1 | 3/2008 | Carpenter | |
| 2008/0114384 A1 * | 5/2008 | Chang | A61B 17/1114 606/153 |
| 2009/0125042 A1 * | 5/2009 | Mouw | A61B 17/1114 606/153 |
| 2009/0312789 A1 * | 12/2009 | Kassab | A61B 17/0057 606/213 |
| 2010/0100167 A1 * | 4/2010 | Bortlein | A61F 2/2436 623/1.11 |
| 2010/0179585 A1 * | 7/2010 | Carpenter | A61F 2/013 606/200 |
| 2011/0202077 A1 * | 8/2011 | Chin | A61B 17/0057 606/153 |
| 2011/0224720 A1 | 9/2011 | Kassab et al. | |
| 2012/0035628 A1 * | 2/2012 | Aguirre | A61B 17/1114 606/153 |
| 2012/0059398 A1 | 3/2012 | Pate et al. | |
| 2013/0324800 A1 * | 12/2013 | Cahill | A61B 17/3423 600/204 |
| 2017/0035425 A1 * | 2/2017 | Fegelman | A61B 17/1114 |
| 2017/0049451 A1 * | 2/2017 | Hausen | A61B 17/115 |
| 2017/0128059 A1 * | 5/2017 | Coe | A61K 31/7036 |

FOREIGN PATENT DOCUMENTS

| | | |
|---|---|---|
| WO | WO 95/17127 | 6/1995 |
| WO | WO 97/47261 | 2/1997 |
| WO | WO 04/096013 | 11/2004 |
| WO | WO 2007/016261 A2 | 2/2007 |
| WO | WO 2011/137224 A1 | 11/2011 |

OTHER PUBLICATIONS

International Search Report of PCT/US 98/10245, dated Sep. 15, 1998.
International Search Report and Written Opinion of PCT/US2015/40041, dated Jan. 14, 2016.
Extended European Search Report in corresponding European Patent Application No. 15819279.9, dated Jan. 31, 2018, in 8 pages.

* cited by examiner

DEVICE AND METHOD FOR ASSISTING END-TO-SIDE ANASTOMOSIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

Disclosed herein are embodiments of a device and method for creating a seal around an opening, such as a tissue opening, and in some embodiments for assisting end-to-side anastomosis.

Description of the Related Art

Currently, the standard practice in performing a coronary artery bypass surgical procedure is to open the patient's chest, place the patient on a cardiopulmonary bypass (heart-lung) machine, stop the heart from beating, and then attach the coronary artery bypass graft(s) to the aorta and coronary arteries. The heart-lung machine is needed to maintain the blood circulation through the patient and to provide gas and heat exchange surfaces. Typically, the blood is cooled using the heart-lung machine to slow down the metabolism of the patient. Additionally, the blood is oxygenated and carbon dioxide is allowed to be released from the blood. The aorta is usually clamped proximal to the entrance point of the blood from the heart-lung machine.

There can be numerous complications with stopping the patient's heart and using a heart-lung machine. For example, the heart-lung machine typically needs to be primed with blood. This is usually done with blood from a blood bank which can be contaminated with infectious agents such as the HIV virus. Further, the heart-lung machine can lyse red blood cells and destroy platelets causing anemia or increasing the risk of hemorrhage. Additionally, the clamping of the aorta can release plaque into the blood stream, which can cause a stroke or a peripheral vascular incident.

Another technique is to partially cross-clamp the aorta with a "U" shaped clamp such that a small blood tunnel is created and an area of blood stasis is created for making a proximal anastomosis site. This technique eliminates the heart-lung machine, but increases the risk of plaque releasing into the blood stream.

SUMMARY

Disclosed herein are embodiments of a device and method for sealing an opening in body tissue. In some embodiments, the device and method may be used to create a seal around an incision or opening in a tissue wall, for example an incision or opening in a blood vessel. In certain embodiments, such devices and methods may be useful to perform an end-to-side anastomosis procedure on the aorta or other blood vessel.

In one embodiment, a device for sealing an opening in body tissue comprises: a hollow elongated member comprising a proximal end and a distal end and having a lumen extending therethrough, wherein the distal end of the hollow elongated member is configured to extend through the opening in the body tissue; shaft member configured to fit within the lumen of the hollow elongated member; and a deformable sealing member coupled to a distal portion of the shaft member at a coupling point, the deformable sealing member comprising a flexible cover portion coupled to the distal portion of the shaft at the coupling point and a sealing ring. The deformable sealing member is configured to move from a first configuration to a second configuration, and from a second configuration to a third configuration. In the first configuration, the deformable sealing member is held within the lumen of the hollow elongated member, wherein the coupling point is located distal to the sealing ring. In the second configuration, the deformable sealing member is positioned distal to and outside of the lumen of the hollow elongated member, and wherein movement of the deformable sealing member from the first configuration to the second configuration causes the sealing ring to enlarge to a dimension larger than that of the hollow elongated member and the flexible cover portion to have generally a cup-like shape with an opening that faces proximally, wherein the sealing ring when enlarged is configured to seal against tissue surrounding the opening in the body tissue. In the third configuration, the deformable sealing member is held within the lumen of the hollow elongated member, wherein the sealing ring is located distal to the coupling point.

In some embodiments, the shaft member can comprise a first portion and a second portion, the first and second portions being removably detached from one another. In some embodiments, the device can be reusable without adding further components.

In some embodiments, the sealing ring can be magnetic. In some embodiments, the device can further comprise a magnetic ring on the outside of the body tissue, wherein the magnetic ring can be configured to magnetically attract the sealing ring so that the deformable sealing member forms a seal around the opening in the body tissue. In some embodiments, the seal can remain without any other forces acting on the deformable member. In some embodiments, the magnetic ring can be attached to the shaft member or the hollow elongated member.

In some embodiments, the deformable sealing member can expand upon distal movement outside of the hollow elongated member. In some embodiments, the hollow elongated member can comprise an internal tapered portion at the distal end configured to facilitate movement of the deformable sealing member from the second configuration to the third configuration. In some embodiments, in the second configuration the sealing ring can be configured to seal against an opening in a blood vessel for creating an anastomosis site.

Also disclosed herein are embodiments of a device for sealing an opening in body tissue, the device comprising a hollow elongated member comprising a proximal end and a distal end and having a lumen extending therethrough, wherein the distal end of the hollow elongated member is configured to extend through the opening in the body tissue. The device further comprises a shaft member configured to fit within the lumen of the hollow elongated member. A deformable sealing member is coupled to a distal portion of the shaft member at a coupling point, the deformable sealing member comprising a magnetic ring and a flexible cover portion, the deformable sealing member configured to form a seal with the body tissue surrounding the opening, wherein the deformable sealing member is moveable from a first configuration within the hollow elongated member to a second configuration wherein the magnetic ring engages a first side of body tissue surrounding the opening. A magnetic portion is configured to be located on a second side of body tissue opposite the first side, wherein the magnetic portion is configured to magnetically attract the magnetic ring, thus forming the seal.

In some embodiments, the magnetic portion can be attached to either the hollow elongated member or the shaft member. In some embodiments, the magnetic portion can be shaped generally the same as the magnetic ring.

Further disclosed herein are embodiments of a method for creating an anastomosis site along a wall of a blood vessel without interrupting the flow of blood through the blood vessel. The method comprises inserting a hollow elongated member through an opening in the wall of the blood vessel. A deformable sealing member located within the hollow elongated member is advanced into the blood vessel, wherein after advancing, the deformable sealing member is located distal to the hollow elongate member and expands from a compressed configuration to an enlarged configuration. The deformable sealing member is moved proximally to create a seal between the deformable sealing member and the wall of the blood vessel, the seal surrounding the opening in the wall of the blood vessel. The deformable sealing member may be removed from the blood vessel by moving the deformable sealing member into the hollow elongated member, wherein the deformable sealing member is inverted when moved into the hollow elongated member.

In some embodiments, after advancing, the deformable sealing member can expand from a compressed configuration to an enlarged configuration having a cup shape with a sealing ring located at a rim of the cup shape. In some embodiments, the method can further comprise enlarging the opening in the wall of the blood vessel after creating the seal. In some embodiments, the method can further comprise suturing a bypass graft to the hole in the blood vessel. In some embodiments, the method can further comprise removing the hollow elongated member from the blood vessel between sutures used to attach the bypass graft to the hole in the blood vessel.

DETAILED DESCRIPTION

Disclosed herein are embodiments of devices that can be used to provide a seal and an anastomosis site for incisions in tissue. Accordingly, an operator could operate on the tissue that is sealed without causing major blood leakage between the inside and outside of the tissue. Advantageously, this can remove the need for certain tools, such as a heart-lung machine, thus reducing the overall risk to the patient. Thus, embodiments of the disclosure can greatly reduce the risks associated with coronary artery bypass surgical procedures.

Specifically, certain embodiments of the devices and methods described herein make use of a flexible, deformable, and optionally reusable member having a generally cup or umbrella shape which can be fit within a catheter, or other elongate tube such as a hypotube, in a compressed, or delivery, configuration. The member can be released in a desired location to expand and seal over an incision in tissue.

As used herein, "cup," "cup-shape," "cup-like shape" and similar language is intended to include any shape, including an umbrella shape, half-sphere shape, pyramidal shape, or cone shape, which forms an enclosed volume with an opening facing away from the enclosed volume. Thus, a generally cup shape includes shapes including, but not limited to rounded, spherical, conical and cylindrical shapes.

Generally, embodiments of the deformable member disclosed herein may be provided on the distal end of a shaft, and both the deformable member and the shaft may be positioned within an elongate tube. This assembly comprising the deformable member, the shaft and the elongate tube may be delivered into an opening in bodily tissue, for example, into the wall of a blood vessel or an artery. Upon the application of a force, for example a distal force away from an operator, the deformable member can exit the tube and open into an enlarged configuration, wherein a cup is formed having an opening which faces proximally toward the shaft to which the flexible member is attached. The shaft can then be advanced proximally (e.g., toward the operator) to draw a rim of the cup against the wall of the artery or other bodily tissue, and thus around the entry point of the shaft and the tube. To withdraw the flexible member, a proximal force can be applied to the shaft, thus withdrawing the deformable member back into the tube in a generally opposite position as when it was inserted. In some embodiments, as the deformable member is withdrawn, the cup-shape of the deformable member is inverted.

While blood vessels/arteries are specifically described below with embodiments of the device, the device may conceivably be used in a variety of other operations involving incisions in blood vessels or organs, or other openings in bodily tissue (whether naturally occurring, abnormal openings, or man-made), and the particular type of tissue is not limiting.

Handle

Figure 1:
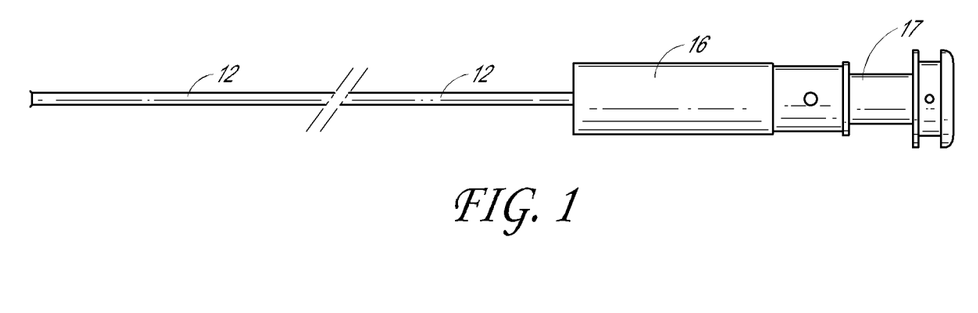
FIG. 1 illustrates a side view of an embodiment of a device for sealing an opening.
Figure 2:
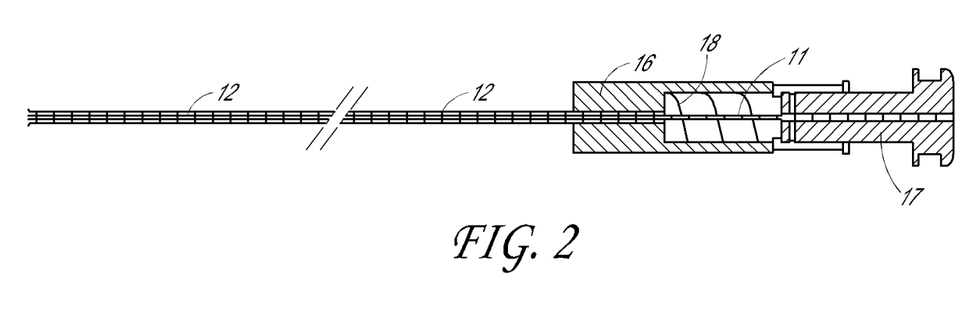
FIG. 2 illustrates a cross-section view of an embodiment of a device for sealing an opening.

FIGS. 1-2 illustrate an embodiment of a device, which in one embodiment, may be an anastomosis assistance device. As shown, a translatable piston 17 can be slidably retained within a handle 16. The handle 16 can be generally hollow and can have sufficient room for the piston 17 to translate through the handle, though the particulars of the handle 16 is not limiting. The handle 16 can allow the operator to have a reference point on when the deformable member 14, or deformable sealing member, has been fully expanded, as discussed below. For example, in some embodiments the handle 16 can include visual, sensory, or auditory clues for the location of the piston 17 within the handle 16. In some embodiments, the handle 16 can include a releasable lock when the piston 17 is in the fully compressed position. In some embodiments, the handle 16 can include grips or projections for ease of holding by an operator.

As shown in the cut-out view of FIG. 2, in some embodiments the handle 16 can also contain a spring 18, which can be located at the distal end of the piston 17. Accordingly, when the piston 17 is translated distally, thereby releasing the deformable member 14 from hollow tube 12, the spring 18 can be put under compression. Upon release of the piston 17, for example upon release of tab 22 from hole 21, the spring 18 can act to press the piston 17 proximally, thereby translating the deformable member 14 proximally back into the hollow tube 12. In some embodiments, a spring 18 is not used, and an operator can pull back on the piston 17.

Attached to the distal center of the handle 16 is a hollow tube 12, or hollow elongated member, having a lumen extending therethrough. The hollow tube 12 can extend distally away from the handle 16. The hollow tube 12 can be formed of either a flexible material, such as a catheter (e.g., a plastic catheter), or can be generally rigid, such as a hypotube. Thus, the hollow tube 12 can be used to guide the translatable shaft 11 discussed below. Further, the hollow tube 12 can be of any desired length or thickness to the operator, depending on the type of application it is used for, and thus the length or thickness is not limiting. In some embodiments, the hollow tube 12 can be swapped out depending on the desired configuration by an operator. The hollow tube 12 may also comprise multiple sections tubing attached or connected to each other, wherein the different sections of tubing may be made of the same or different materials. The hollow tube 12 may not be moved by translation of the piston 17, and thus can remain stationary with respect to the handle 16.

A translatable shaft 11, or wire, can be attached to the center of the piston 17 and can extend distally away from the handle 16 and piston 17. Thus, motion of the piston 17 can translate the translatable shaft 11 through the hollow tube 12 and into a desired location in a patent. The distal end of the translatable shaft 11 can be attached to the deformable member 14, as further discussed in detail below. The translatable shaft 11 can traverse through a lumen of the hollow tube 12. In some embodiments, the translatable shaft 11 can be made out of a durable material such as stainless steel or plastic. In some embodiments, the translatable shaft 11 can be relatively rigid, and thus can be configured to translate the deformable member 14 as the piston 17 is translated. In some embodiments, the translatable shaft 11 can be flexible in order to follow any curvature of the hollow tube 12. In some embodiments, the translatable shaft 11 can be longer than the hollow tube 12, thus allowing the deformable member 14 to move in and out of the hollow tube 12 upon application of a force on the translatable piston 17.

While the above describes the use of a handle, spring, and piston configuration, other types of configurations can be used with the disclosure and the above configuration does not limit the disclosure. For example, a physician could physically hold the hollow tube 12 and translatable shaft 11 without the handle 16, and thus the handle 16 could be optional. Further, in some embodiments the hollow tube 12 and translatable shaft 11 can be connected to electronic components which can automatically move the translatable shaft 11, or an operator can operate the electronic components. For example, a button or switch could be used to actuate the translatable shaft 11.

Deformable Member

Figure 3:
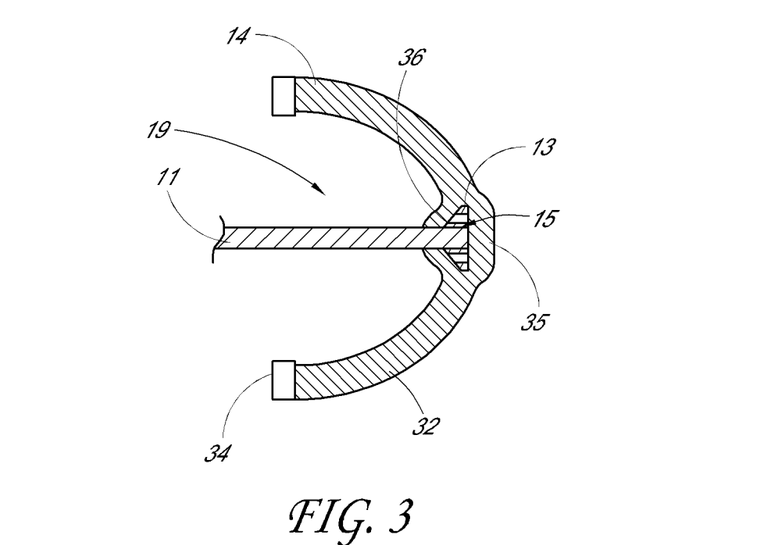
FIG. 3 illustrates a cross-sectional side view of an embodiment of a deformable member.

A deformable member 14 can be attached to a distal end of translatable shaft 11 in order to provide a seal around a tissue opening. As shown in FIG. 3, the deformable member 14 can be formed generally from two components, a membrane 32 and ring 34, though other components can be used as well. Further, the membrane 32 and ring 34 can be one integrally formed component, or can be made of a plurality of other components.

Figure 4:
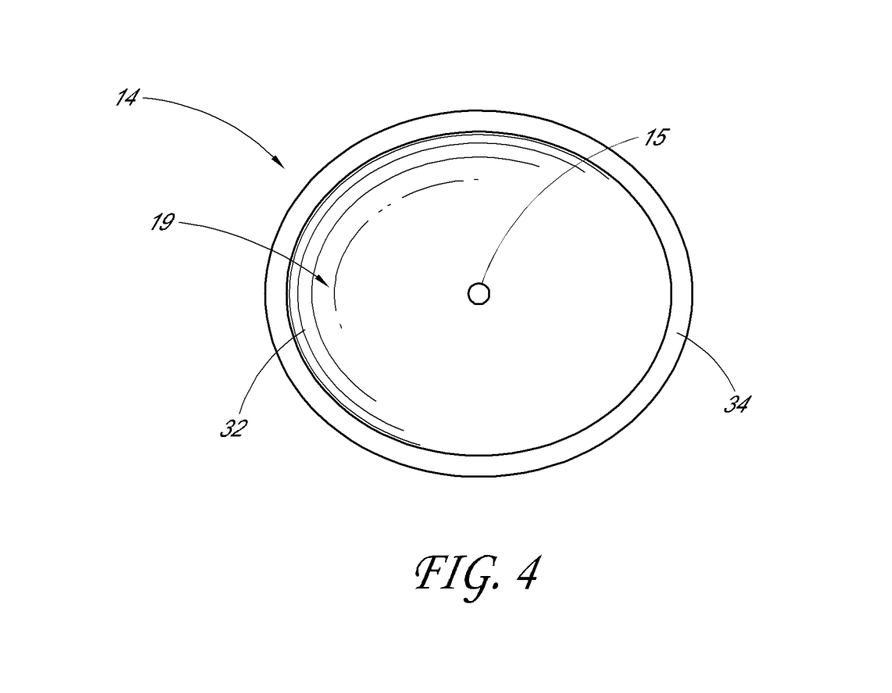
FIG. 4 illustrates a proximal to distal view of an embodiment of a deformable member.

FIGS. 3-4 show the deformable member 14 in the enlarged configuration (e.g. the expanded or deployed position), which is the position the deformable member 14 would be when forming a seal around a tissue incision. In some embodiments, the deformable member 14 can be formed from a flexible cover material, such as membrane 32, generally surrounding and/or attached to a body portion such as a sealing ring 34.

The ring 34 can be generally more rigid than that of the membrane 32, though the ring 34 can still be sufficiently flexible to fit within the hollow tube 12. Thus, the ring 34 can provide shape stability to the ring 34. The ring 34 can be configured to bend when a compressive stress is applied, and then return to its original shape upon the removal of the compressive stress. Thus, the ring 34 can be self-expanding. The ring 34 can be formed of a more rigid biocompatible material, such as a metal or plastic, though can still be flexible enough to fit within hollow tube 12. In some embodiments, the ring 34 can be a wire frame. In some embodiments, the ring 34, can be a thickened or less flexible portion of the membrane 32, and thus can be essentially the same material as the membrane 32.

Figure 11:
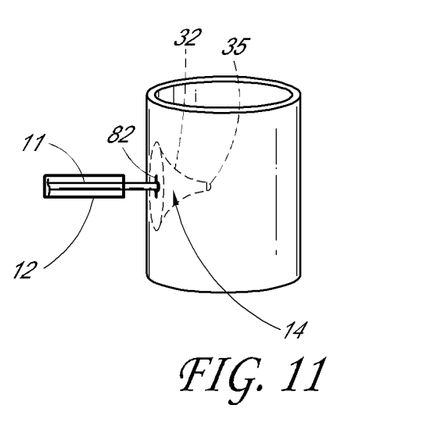
FIG. 11 illustrates a deformable member inserted into a blood vessel after expansion.

The membrane 32 can form a cup-like configuration upon full expansion, as shown in the cross-section of FIG. 3, with the ring 34 located at the rim of the cup-shaped membrane. The cup-like configuration can be, for example, an umbrella-like configuration. In some embodiments, the cup-like configuration may not have a convex outer surface, but could also have straight surfaces or concave surfaces (such as shown in FIG. 11). As shown, the cup-like configuration can form a cavity 19 (anastomosis site) in which an operator can operate on without excessive blood loss. The membrane 32 can be formed of a single piece of material, or may comprise multiple pieces of material, and may further comprise supports that help hold the shape of the membrane when expanded. Similar to the ring 34, the membrane 32 can be compressed into a small shape upon the application of a compressive force. Upon removal of the compressive force, the membrane 32 can return to its original shape, and can thus be self-expanding. In some embodiments, the membrane 32 is not self-expanding and expands based on the ring 34. The membrane 32 can be made out of a flexible compliant biocompatible material such as, for example, polyurethane, Dynaflex, or silicone, and the type of material is not limiting.

In some embodiments, the membrane 32 can be made from a flexible braided tube or sleeve, such as with one-quarter inch expandable mesh. In some embodiments, the entire deformable member 14 can be coated with a flexible, impermeable material, such as silicone, to make the deformable member 14 impermeable to the flow of blood. In some embodiments, the silicone coating may alternatively be applied to only a distal half or two-thirds of the deformable member 14. The particular portion of the deformable membrane 14 covered by silicone is not limiting. In some embodiments, the membrane 32 is solid so that blood cannot flow through.

In some embodiments, the ring 34 and membrane 32 can be formed of the same material. In some embodiments, the ring 34 and membrane 32 can be integrally formed. In some embodiments, the ring 34 can be attached to the membrane 32 through, for example, adhesive or sewing, though the type of attachment is not limiting. In some embodiments, the ring 34 is no more than the edge of the membrane 32.

As shown in the cutout viewpoint of FIG. 3, the translatable shaft 11 can be inserted into the middle of the cup-shaped membrane 32. Specifically, the translatable shaft 11 can be connected to the distal end 35 of the membrane 32 at a coupling point 15. In some embodiments, as shown in FIG. 3, the translatable shaft 11 can have an expanded distal tip 13, such as an arrow or mushroom shaped tip, which can fit within a slot 36 at the distal end 35 of the deformable member 14. In some embodiments, the translatable shaft 11 can be permanently attached to the deformable member 14. In some embodiments, the translatable shaft 11 can be removable attached to the deformable member 14. In some embodiments, an adhesive can be used to connect the translatable shaft 11 to the membrane 32. In some embodiments, physical forces, such as friction, can be used to connect the translatable shaft 11 to the membrane 32. Thus, an adhesive may not be used in some embodiments. The attachment means is not limiting.

FIG. 4 shows a viewpoint looking into the cup-shaped membrane 32 towards the distal end 35 of the deformable member 14. As shown, the ring 34 can be generally circular in shape, though other configurations, such as squares or ovals, can be used, and the shape is not limiting.

Figure 5:
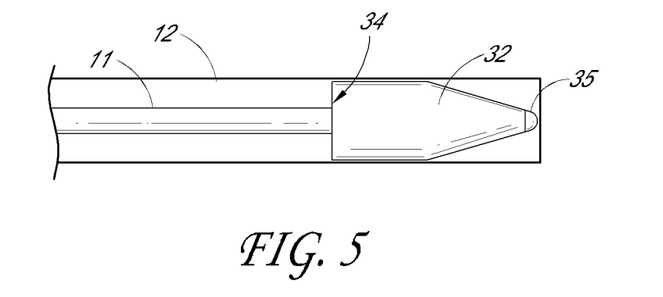
FIG. 5 illustrates a compressed first configuration of an embodiment of a deformable member.
Figure 6:
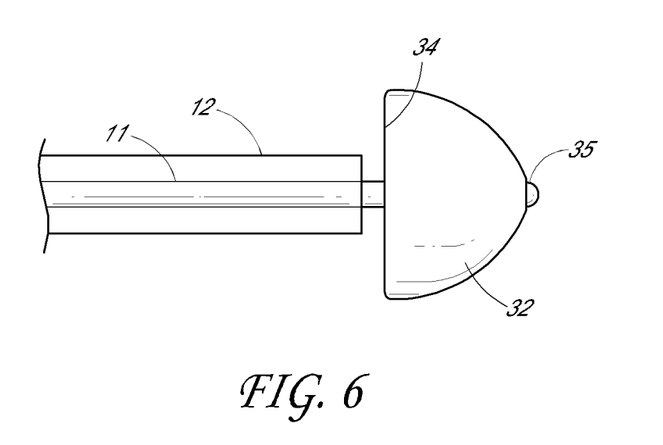
FIG. 6 illustrates an open or expanded second configuration of an embodiment of a deformable member.
Figure 7:
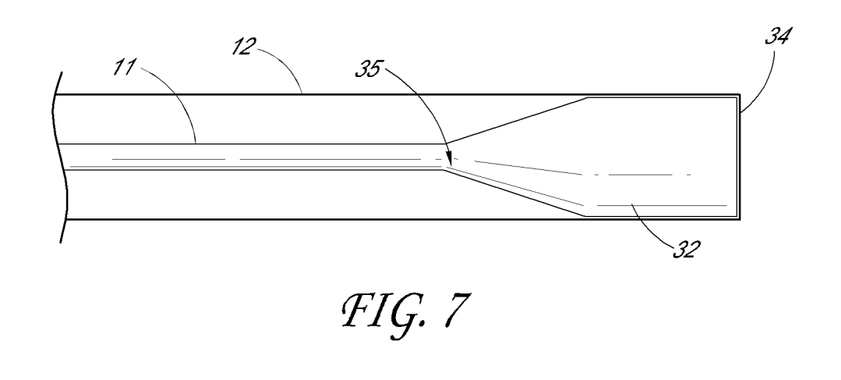
FIG. 7 illustrates a closed third configuration of an embodiment of a deformable member.

FIGS. 5-7 shows the deformable member 14 in different configurations which would generally occur during use of embodiments of the device. As shown, the hollow tube 12 can radially compress the deformable member 14 in FIGS. 5 and 7, thus forming the particular shape.

FIG. 5 illustrates a first configuration of the deformable member 14 as it can look inside of the hollow tube 12 prior to expansion in a blood vessel or other body location. As shown, the membrane 32 and ring 34 are radially compressed by the hollow tube 12, allowing the deformable member 14 to fit within, and slide within, the hollow tube 12. In some embodiments, a lubricant can be used on the inner surface of the hollow tube 12. In some embodiments, the deformable member 14 could be compressed even further than what is shown in FIG. 5, so that the diameter of the deformable member 14 is approximately that of the translatable shaft 11. Thus, the deformable member 14 would be able to fit into very small incision spaces. As shown, in this compressed configuration, the distal end 35 (and the coupling point 15) of the deformable member 14 is distal to the ring 34.

FIG. 6 illustrates a second configuration of the deformable member 14 upon release from the hollow tube 12. As shown, the member 14 achieves a generally cup-like configuration upon expansion, with the ring 34 expanding out to its full diameter. The member 14 can in one embodiment expand without any outside force, and thus can expand purely based on the release of the compression from the hollow tube 12. In other embodiments, a mechanism may be included that holds the deformable member in its collapsed configuration even after being released from hollow tube 12, which allows the deformable member 14 to expand after it has been moved relatively distally out of the hollow tube 12. As shown, when expanded, the deformable member 14 can have the same orientation as shown in FIG. 5. Thus, as illustrated in FIG. 6, the coupling point 15 between the translatable shaft 11 and the deformable member 14 is still located distal to the ring 34.

FIG. 7 illustrates a third configuration of the deformable member 14 as it would look inside of the hollow tube 12 when withdrawn into the hollow tube 12 after expansion in the blood vessel or other body location, discussed below. As shown, the configuration and/or orientation is generally opposite of that shown in FIG. 5, with the ring 34 being distal to the membrane 32 and the cup-shaped member being inverted. Therefore, the distal end 35 (and coupling point 15) of the deformable member 14 is proximal to the ring 34.

After removal from the blood vessel or other body location, the deformable member 14 can be reoriented by an operator back into its original position, and can be relocated within the hollow tube 12 for further use, or it may be disposed. Thus, in some embodiments the device can be reusable. In some embodiments, the device may be able to handle different sterilization procedures.

Method of Use

One embodiment of the disclosed device can be used for bypassing of blood vessels and arteries. Discussed in detail below is a configuration used for coronary artery bypass grafting, though embodiments of the disclosed device can be used with other vessels and organs as well, and with other bodily openings, and the disclosed method is not limited to the particular procedure described below.

Figure 8:
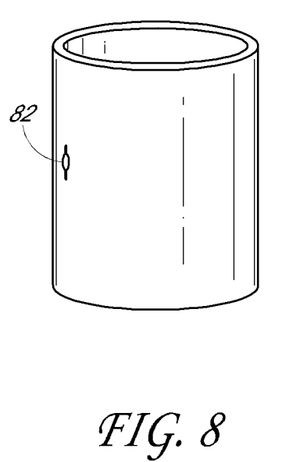
FIG. 8 illustrates an incision formed in a blood vessel.

In coronary artery bypass grafting, a patient can be prepped and access to the aorta can be established by either an open chest procedure, port access, or via a small lateral incision in the ribs. As shown in FIG. 8, once the aorta is accessed, a small incision 82 can be made in a blood vessel, such as the aorta, at a proximal anastomosis site for a coronary artery bypass procedure. If the incision 82 is not sealed, blood will continuously leak out, leading to potential complications during the surgery.

Figure 9:
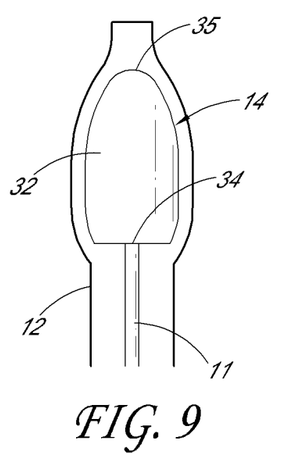
FIG. 9 illustrates a configuration of an embodiment of a deformable member in a deformable hollow tube.

As shown in FIG. 9, the deformable member 14 can first be located within the hollow tube 12. FIG. 9 shows that the hollow tube 12 expands around where the deformable member 14 is located. However, in some embodiments the hollow tube 12 would not necessarily change dimensions based on the location of the deformable member 14. This is especially true when a more rigid tube is used, such as a hypotube, as compared to a catheter. As shown, the member 14 in the hollow tube 12 has a shape generally similar to that shown in FIG. 5.

Figure 10:
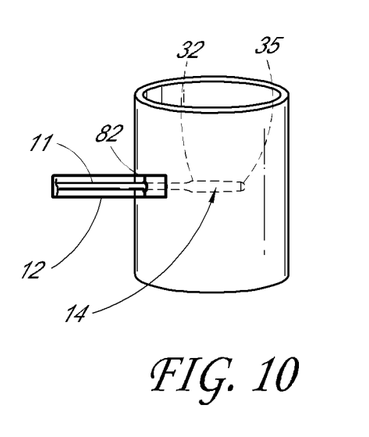
FIG. 10 illustrates a deformable member inserted into a blood vessel prior to expansion.

As shown in FIG. 10, the distal end of hollow tube 12 containing the deformable member 14 and translatable shaft 11 can be inserted through a hole 82 in a blood vessel so that the distal opening of the hollow tube 12 is located in the blood vessel. Upon insertion of the end of the hollow tube 12, the deformable member 14 can be released from the opening of the hollow tube 12. This can be done in a number of different ways, none of which are limiting. In some embodiments, the hollow tube 12 can be pulled out of the blood vessel by a proximal force, while the deformable member 14 and translatable shaft 11 can be located and held in the same position. In some embodiments, the deformable member 14 can be pushed out of the hollow tube 12 through a distal force applied on the translatable shaft 11. Once released, the hollow tube 12 can then be pulled back from the blood vessel by a proximal force (shown in FIG. 11). FIG. 10 shows the deformable member 14 prior to expansion in the blood vessel, but after being partially released from the hollow tube 12. In some embodiments, the deformable member 14 may already be expanding in this position, and thus may be partially expanded.

Upon release, the deformable member 14 can expand into an umbrella, or cup, shape which can cover up the incision 82 made in the blood vessel as shown in FIG. 11. As shown, the hollow tube 12 can be pulled back from the blood vessel. Accordingly, the deformable member 14 can be located on the interior of the blood vessel. An operator can then apply proximally directed tension to the deformable member 14 to seal the edges or the rim of the deformable member 14 to the inner wall of the blood vessel. In some embodiments, the deformable member 14 only occludes the area of the aorta around the incision 82 and does not otherwise obstruct the flow of blood in the aorta. Blood flows from the heart, past the distal end of the deformable member 14, and to the peripheral tissues. Thus, the deformable member 14 prevents blood from escaping the surgical site but does not require the heart to be stopped. The operator can then operate on the area covered by the deformable member 14.

Figure 12:
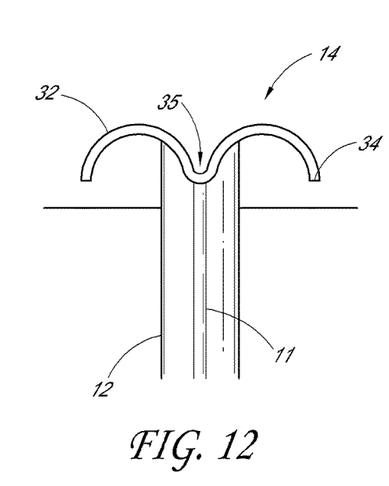
FIG. 12 illustrates an embodiment of a deformable member partially withdrawn within a hollow tube.
Figure 13:
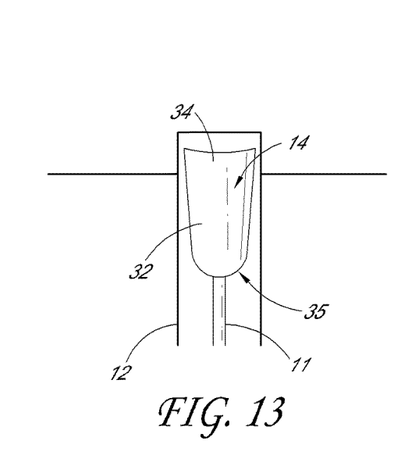
FIG. 13 illustrates an embodiment of a deformable member fully withdrawn within a hollow tube.

When the operator desires the deformable member 14 to be removed, the hollow tube 12 can be inserted back into the blood vessel through the incision. In some embodiments, the hollow tube 12 does not enter the blood vessel, but remains outside or in line with the wall of the blood vessel. The deformable member 14 can then be positioned back within the hollow tube 12. In some embodiments, the hollow tube 12 can be pushed into the blood vessel while the member 14 remains in the same location. This causes the deformable member 14 to fold around and be brought into the hollow tube 12, as shown in FIG. 12. In some embodiments, the hollow tube 12 remains stationary and a proximal force is applied to the translatable shaft 11, thus bringing the deformable member 14 into the hollow tube 12. In some embodiments, the deformable member 14 is brought fully within the hollow tube 12. In some embodiments, the deformable member 14 is brought partially within the hollow tube 12. Upon entering the hollow tube 12, the deformable member 14 is generally in the opposite position (e.g., inverse position) as when it was first inserted into the blood vessel, as shown in FIG. 13.

Figure 14:
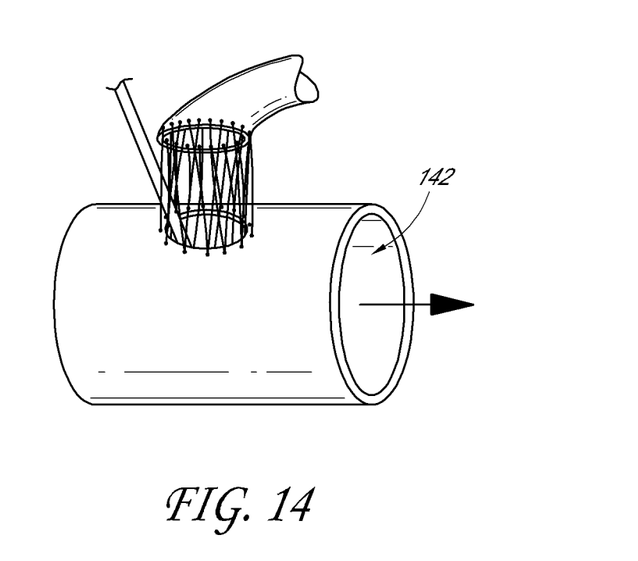
FIGS. 14-15 illustrate the suturing of a blood vessel graft and removal of a deformable member.
Figure 15:
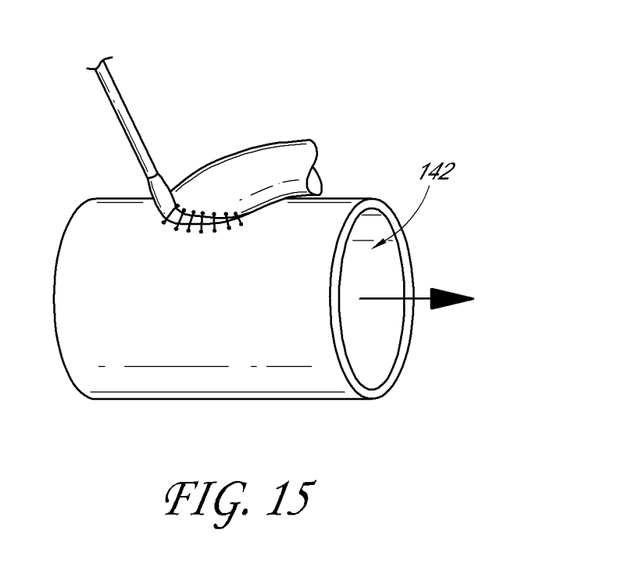

When the deformable member 14 is located inside the blood vessel, the ring 34 of the member 14 can rest against the surface of the blood vessel (the inner surface of the vessel in FIG. 14, shown as element 142). Therefore, the incision 82 can be sealed from the path of the blood in the blood vessel, preventing blood from leaking out of the blood vessel. Once the seal has been formed to provide a working area, the operator can widen the incision as needed to create a proximal anastomosis site for a coronary bypass graft. The operator then can loosely suture one end of a coronary artery bypass graft (typically a section of a saphenous vein) to the hole, shown in FIG. 14. The operator can allow enough slack on the suture to be able to remove the device (at this point the hollow tube 12, including the deformable member 14), as shown in FIG. 15.

The operator can then remove the hollow tube 12 from the aorta around the loose sutures and pulls the sutures around the graft tight to give the graft a good seal. The other end of the coronary artery bypass graft can be attached to a surgically created hole in a coronary artery while the heart is still beating before, during, or after the aortic anastomosis. The rest of the coronary bypass procedure can be completed using standard techniques.

Tube Configuration

Figure 16:
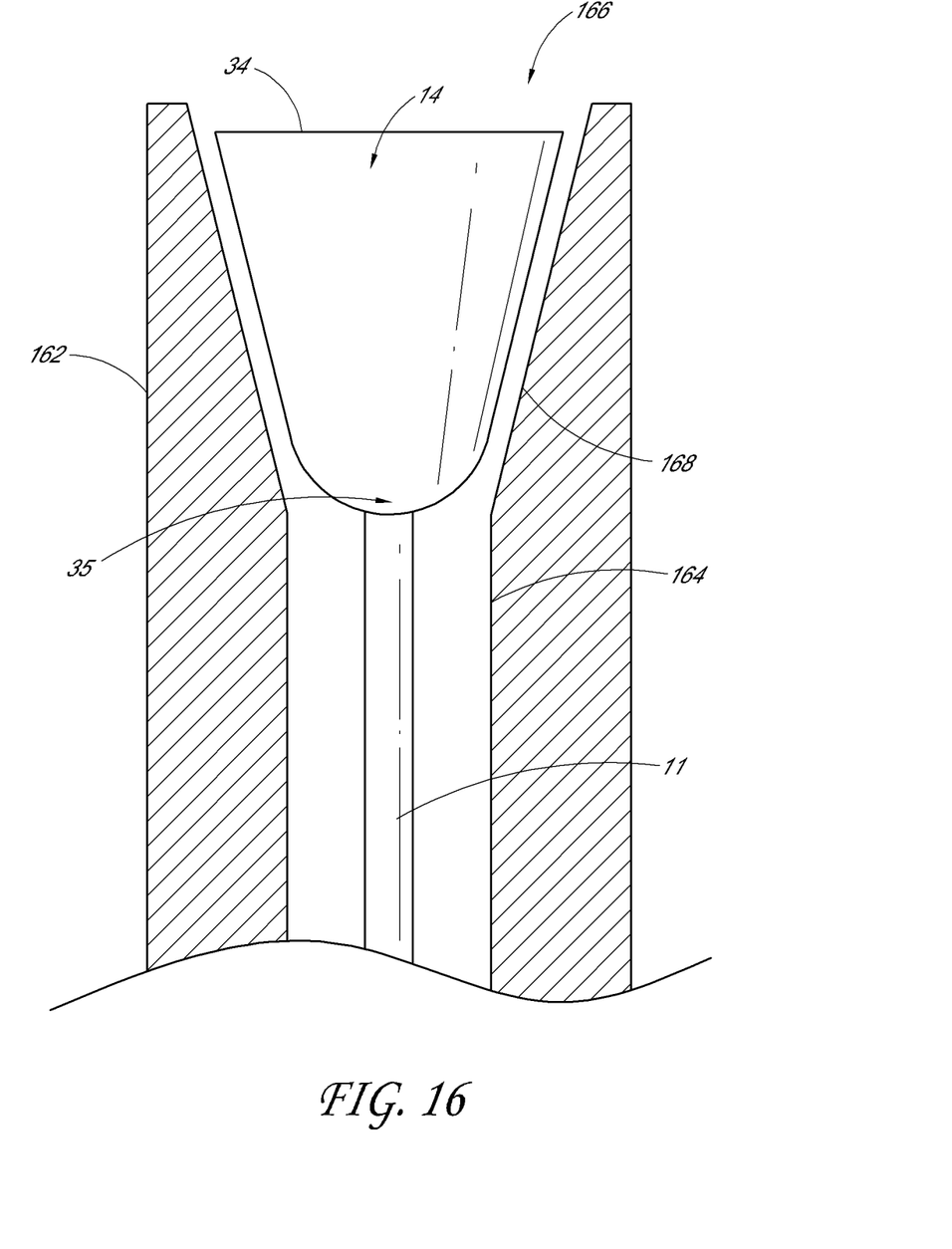
FIGS. 16-17 illustrate embodiments of the internal structure of a tube.
Figure 17:
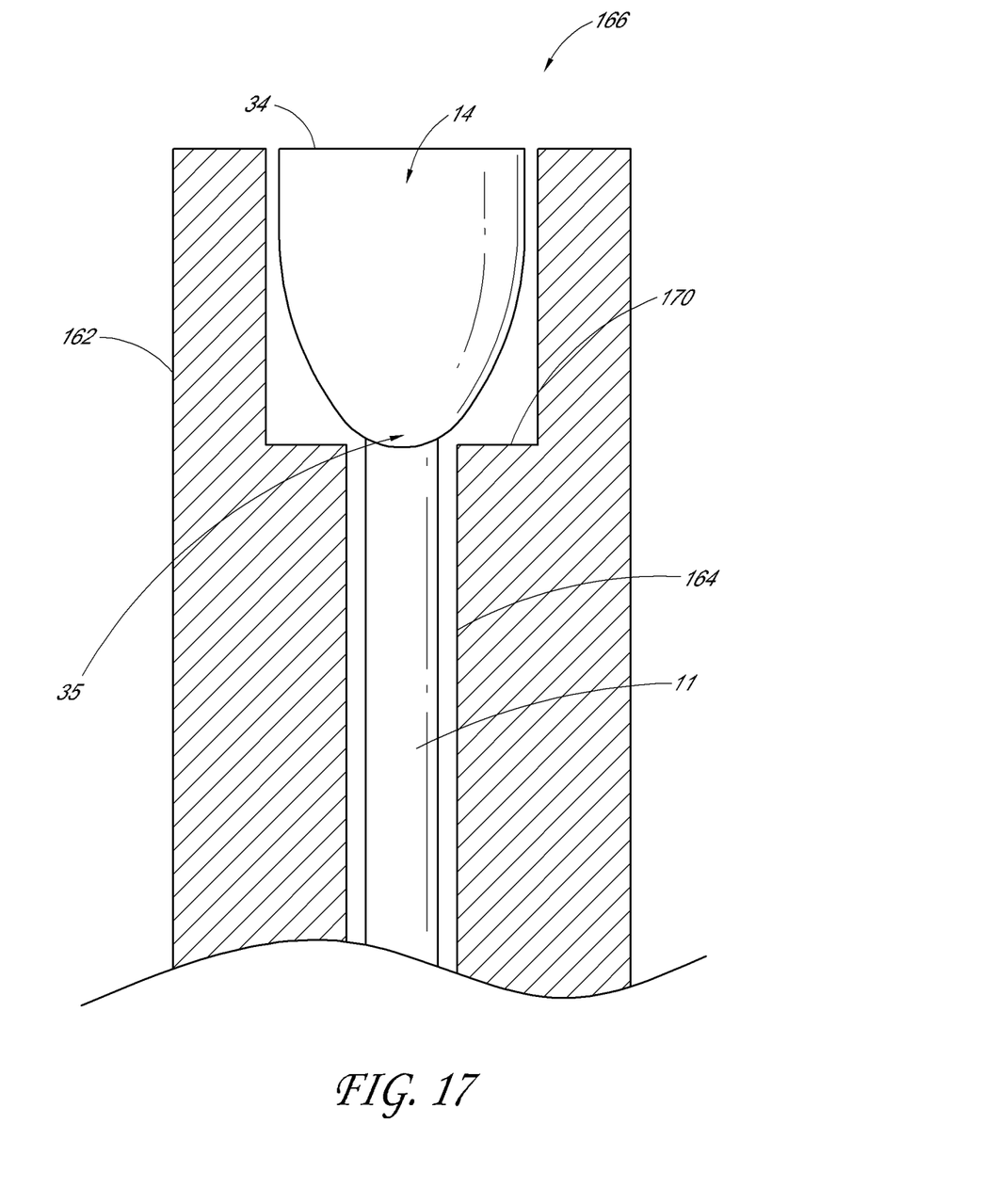

FIG. 16 illustrates an example embodiment of the hollow tube 12. As shown, the hollow tube 12 can have an outer wall 162 and an inner wall 164 spaced away from the outer wall 162. Near the distal opening 166, a generally tapered surface 168 can extend from the inner wall 164 to the outer wall 162. This tapered surface 166 can help direct and position the deformable member 14 when being pushed in or out of the hollow tube 12, and can prevent the deformable member 14 from catching. In some embodiments, the surface between the outer wall 164 and the inner wall 162 need not be tapered, and the surface can be formed of generally straight edges with steps 170, as shown in FIG. 17. In some embodiments, the edges are generally curved. In some embodiments, the hollow tube 12 can be a standard catheter or hypotube, and thus no steps or tapers may be used.

Figure 18:
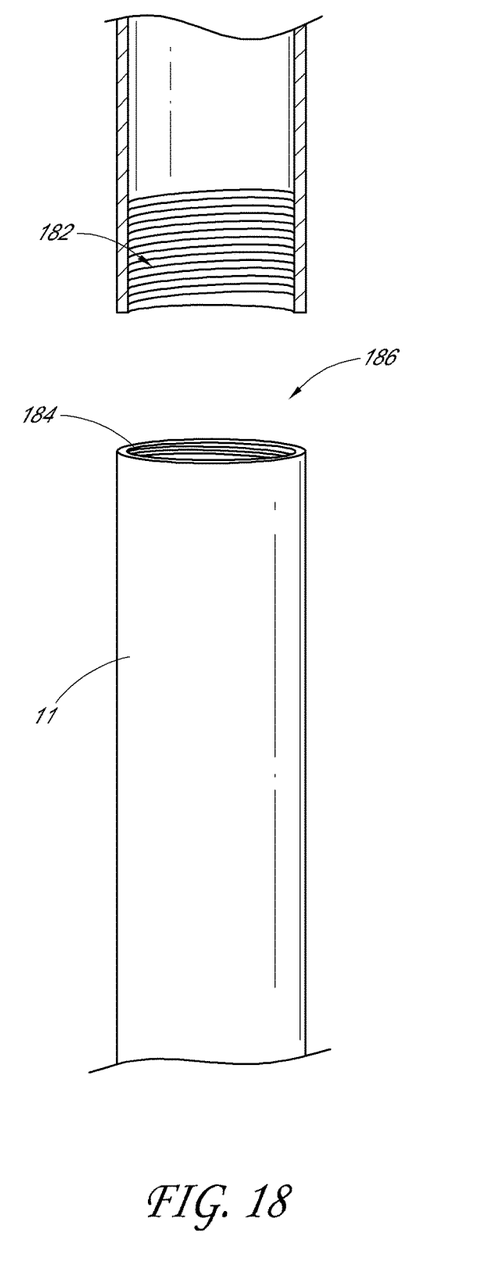
FIG. 18 illustrates an embodiment of a detachable shaft.

In some embodiments, the hollow tube 12 and/or the translatable shaft 11 can be detachable, as shown in FIG. 18, at a detachable section 186. Accordingly, the piston 17 and handle 16, along with a portion of the hollow tube 12 and the translatable shaft 11 can be withdrawn from the portion having the deformable member 14. The detachable section 186 can be located anywhere along the translatable shaft 11 and/or hollow tube 12. In some embodiments, only the translatable shaft 11 is detachable, and the hollow tube 12 can be drawn away from the deformable member 14, thus leaving a portion of the translatable shaft 11 and the deformable member 14 inside a patient. This can allow more maneuverability for an operator of the device as there are fewer parts that would be in the way during an operation. Upon completion of whatever procedure an operator is performing, the pieces can be reattached, and thus the procedure for withdrawing the deformable member 14, as discussed above, can take place.

The attachment of the portions of the translatable shaft 11 and/or hollow tube 12 are not limiting, and different attachment means can be used. In some embodiments, male and female screw portions 182/184 can be used, as shown in FIG. 18. In some embodiments, snaps, hooks, friction, or other means of detachable attachment can be used. In some embodiments, the portions can be reattached just by using the handle 16. In some embodiments, an operator can directly attach the portions by holding onto both portions and connecting them.

Magnetic Deformable Member

Figure 19:
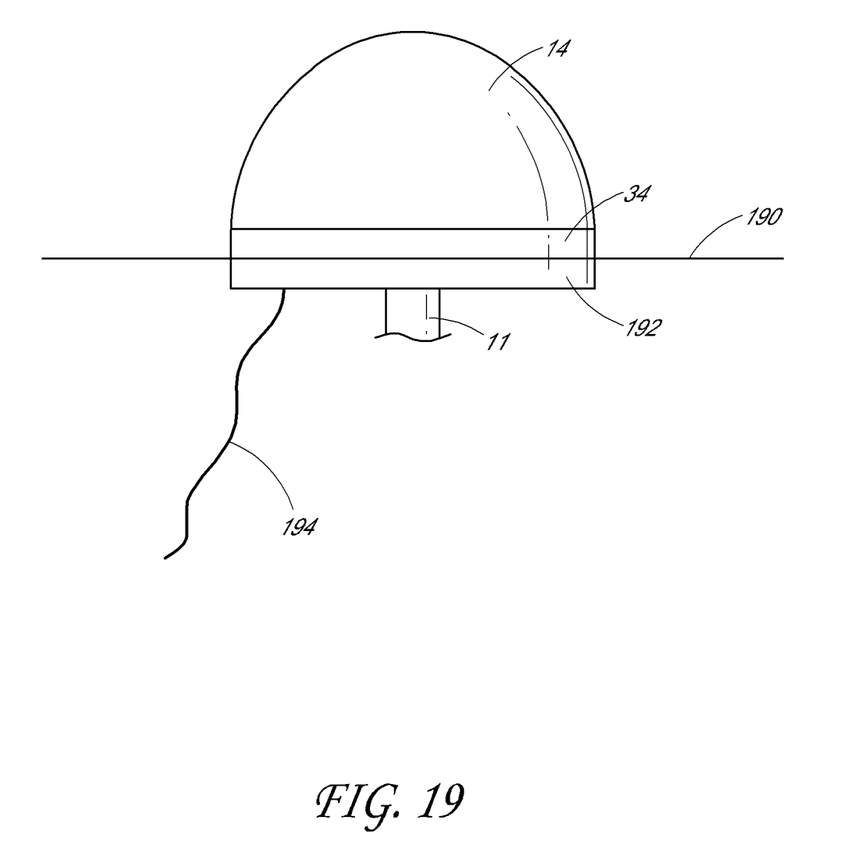
FIG. 19 illustrates an embodiment of a magnetic deformable member.

In some embodiments, magnetism can be used to hold the deformable member 14 onto a blood vessel. FIG. 19 shows an example of such a configuration in a blood vessel 190. As discussed above, the deformable member 14 can comprise a generally circular, flexible ring 34 configured to expand into the cup shape upon removal of all outside forces. In some embodiments, the ring 34 can be formed of a magnetic material, such as a magnetic metal, and the type of magnetic material is not limiting.

Outside of the blood vessel 190, the device can have an outer magnetic portion 192 having a magnetic material configured to attract the magnetic material in the ring 34 of the deformable member 14. In some embodiments, the outer magnetic portion 192 may be generally sized to mirror the size and shape of the ring 34. In some embodiments, the outer magnetic portion 192 may be substantially larger than the ring 34, thus facilitating magnetic response even if perfect alignment is not made. In some embodiments, the outer magnetic portion 192 may be separate from the translatable shaft 11 and/or hollow tube 12. Therefore, upon insertion and expansion of the deformable member 14, the outer magnetic portion 192 may be placed outside the blood vessel 190. For example, the outer magnetic portion 192 may be ring shaped with a hinge or gap, wherein the outer magnetic portion 192 can surround the translatable shaft 11, and the hinge can be closed. In some embodiments, the outer magnetic 192 portion may be connected to the translatable shaft 11 and/or hollow tube 12.

Upon placement of the outer magnetic portion 192 onto the blood vessel 190 in a location corresponding to the ring 34 of the deformable member 14, the magnetic attraction between the pieces can be sufficient as to form a fluid tight seal on the inside of the blood vessel 190, thus preventing blood from escaping through the incision. Thus, an operator need not keep providing a proximal force to the deformable member 14 to keep the deformable member 14 in place, allowing an operator free use of both hands. This can be especially advantageous for embodiments where the translatable shaft 11 can be disconnected into two portions, as described above. Thus, numerous components can be removed and moved out of the way so that an operator can perform actions with less equipment. Further, the outer magnetic portion 192 can act as a guide so that an operator does not suture into the deformable member 14 during operation.

In some embodiments, the outer magnetic portion 192 can be attached to a removal element 194. This removal element 194 can be, for example, a string or rod. Accordingly, when an operator desires to remove the deformable member 14 from the blood vessel 190, the operator can provide a force on the removal element 194 away from the blood vessel 190, thus overcoming the magnetic attraction between the deformable member 14 and the outer magnetic portion 192. Upon removing the outer magnetic portion 192, the deformable member 14 can be removed from the blood vessel 190 as discussed in the procedures above. The removal element 194 can also be used to help locate the outer magnetic portion 192 if it were to become unattached. In some embodiments, the removal element 194 can attach the outer magnetic portion 192 to either the translatable shaft 11 or the hollow tube 12, therefore keeping all components together.

Embodiments of the disclosed device can provide for numerous advantages. Because the device can be inserted and removed from the blood vessel without damaging any of the components, it can be used at multiple sites during a surgery. This can be especially advantageous as many operations require numerous anastomosis sites. As the device is reusable, this can reduce the overall costs of a procedure in comparison to other devices which, for example, unravel during use and cannot be used again.

In some embodiments, the above disclosed configuration can be used with a hole punch device, as described in detail in U.S. Pat. No. 6,409,739, hereby incorporated by reference in its entirety. Additionally, other components described in detail in U.S. Pat. No. 6,409,739 can be used with configurations of the above device as well.

From the foregoing description, it will be appreciated that an inventive product and approaches for medical devices are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A device for sealing an opening in body tissue, the device comprising:
   a hollow elongated member comprising a proximal end and a distal end and having a lumen extending therethrough, wherein the distal end of the hollow elongated member is configured to extend through the opening in the body tissue;
   a shaft member configured to fit within the lumen of the hollow elongated member; and
   a deformable sealing member coupled to a distal portion of the shaft member at a coupling point, the deformable sealing member comprising a flexible cover portion coupled to the distal portion of the shaft member at the coupling point and a sealing ring, wherein the sealing ring is magnetic;
   wherein the deformable sealing member is configured to move from a first configuration to a second configuration, and from the second configuration to a third configuration, wherein:
      in the first configuration, the deformable sealing member is held within the lumen of the hollow elongated member, wherein the coupling point is located distal to the sealing ring;
      in the second configuration, the deformable sealing member is positioned distal to and outside of the lumen of the hollow elongated member, and wherein movement of the deformable sealing member from the first configuration to the second configuration allows the sealing ring to enlarge to a dimension larger than that of the hollow elongated member, the flexible cover portion having generally a cup-like shape forming a cavity with an opening that faces proximally, wherein the sealing ring when enlarged is configured to seal against body tissue surrounding the opening in the body tissue and the cavity defines an anastomosis site; and
      in the third configuration, the deformable sealing member is held within the lumen of the hollow elongated member, wherein the sealing ring is located distal to the coupling point; the device further comprising a magnetic ring on the outside of the body tissue, wherein the magnetic ring is configured to magnetically attract the sealing ring so that the deformable sealing member forms a seal around the opening in the body tissue; wherein the magnetic portion is attached to a removal element, and wherein the magnetic portion and the removal element are configured to be detached by a force on the removal element away from the deformable sealing member.

2. The device of claim 1, wherein the shaft member comprises a first portion and a second portion, the first and second portions being removably detached from one another.

3. The device of claim 1, wherein the device is reusable without adding further components.

4. The device of claim 1, wherein the seal remains without any other forces acting on the deformable member.

5. The device of claim 1, wherein the magnetic ring is attached to the shaft member or the hollow elongated member.

6. The device of claim 1, wherein the deformable sealing member expands upon distal movement outside of the hollow elongated member.

7. The device of claim 1, wherein the hollow elongated member comprises an internal tapered portion at the distal end configured to facilitate movement of the deformable sealing member from the second configuration to the third configuration.

8. The device of claim 1, wherein the magnetic ring is separate from the shaft member.

9. The device of claim 1, wherein the flexible cover portion of the deformable sealing member is permanently coupled to the distal portion of the shaft member at the coupling point.

10. A device for sealing an opening in body tissue, the device comprising:
    a hollow elongated member comprising a proximal end and a distal end and having a lumen extending therethrough, wherein the distal end of the hollow elongated member is configured to extend through the opening in the body tissue;
    a shaft member configured to fit within the lumen of the hollow elongated member;
    a deformable sealing member permanently coupled to a distal portion of the shaft member at a coupling point, the deformable sealing member comprising a magnetic ring and a flexible cover portion, the deformable sealing member configured to form a seal with the body tissue surrounding the opening, wherein the deformable sealing member is moveable from a first configuration within the hollow elongated member to a second configuration wherein the magnetic ring engages a first side of body tissue surrounding the opening; and
    a magnetic portion configured to be located on a second side of body tissue opposite the first side, the magnetic portion being separate from the shaft member, wherein the magnetic portion is configured to magnetically attract the magnetic ring, thus forming the seal; wherein the magnetic ring is attached to a removal element, and wherein the magnetic ring and the removal element are configured to be detached by a force on the removal element away from the deformable sealing member.

11. The device of claim 10, wherein the magnetic portion is attached to either the hollow elongated member.

12. The device of claim 10, wherein the magnetic portion is shaped generally the same as the magnetic ring.

13. The device of claim 10, wherein in the first configuration, the deformable sealing member is held within the lumen of the hollow elongated member, wherein the coupling point is located distal to the sealing ring.

14. The device of claim 13, wherein the deformable sealing member is configured to move from the second configuration to a third configuration, in which the deformable sealing member is held within the lumen of the hollow elongated member, wherein the sealing ring is located distal to the coupling point.

15. The device of claim 10, wherein the flexible cover portion has generally a cup-like shape forming a cavity with an opening that faces proximally, wherein the cavity defines an anastomosis site in the second configuration.

16. The device of claim 10, wherein movement of the deformable sealing member from the first configuration to the second configuration allows the magnetic ring to enlarge to a dimension larger than that of the hollow elongated member.

* * * * *

UNITED STATES PATENT AND TRADEMARK OFFICE
CERTIFICATE OF CORRECTION

PATENT NO. : 10,178,993 B2
APPLICATION NO. : 14/795146
DATED : January 15, 2019
INVENTOR(S) : Anthony A. Nobles et al.

It is certified that error appears in the above-identified patent and that said Letters Patent is hereby corrected as shown below:

In the Claims

In Column 14 at Line 44, in Claim 11, change "to either" to --to--.

Signed and Sealed this
Twenty-third Day of April, 2019

Andrei Iancu
*Director of the United States Patent and Trademark Office*